United States Patent [19]

Hevesy

[11] 3,949,747

[45] Apr. 13, 1976

[54] BIOPSY SET

[76] Inventor: William K. Hevesy, 2417 E. LaPalma Ave., Anaheim, Calif. 92806

[22] Filed: Oct. 3, 1974

[21] Appl. No.: 511,534

[52] U.S. Cl. .................. 128/2 B; 128/310; 206/375
[51] Int. Cl.² .......................................... A61B 10/00
[58] Field of Search ........................... 128/2 B, 310; 206/375–378

[56] References Cited
UNITED STATES PATENTS

| 248,958 | 11/1881 | Starr | 32/40 R X |
|---|---|---|---|
| 1,712,473 | 5/1929 | McWethy | 206/378 |
| 2,180,572 | 11/1939 | White | 206/375 |
| 2,451,133 | 6/1969 | Hathaway et al. | 32/40 R X |
| 2,522,213 | 9/1950 | Doniger | 206/375 |
| 3,512,519 | 5/1970 | Hall | 128/2 B |
| 3,726,393 | 4/1973 | Thompson | 206/378 |
| D167,868 | 9/1952 | Selikoff et al. | 206/378 X |

FOREIGN PATENTS OR APPLICATIONS

| 152,120 | 6/1904 | Germany | 206/375 |
|---|---|---|---|
| 1,316,639 | 12/1962 | France | 206/375 |

OTHER PUBLICATIONS

*Journ. of Amer. Med. Assoc.*, May 10, 1913, p. 2405.

*Primary Examiner*—Kyle L. Howell
*Attorney, Agent, or Firm*—Allen A. Dicke, Jr.

[57] ABSTRACT

Set is formed of base, punches, probe, and handle. The base has a plurality of receptacles, each for receiving, restraining and protecting the cutting edge of a tissue biopsy punch. Each punch is engageable by a handle, which can be stored in the base when not in use. The set thus becomes a structure which holds and protects the sharp punches, probe and handle during sterilization and afterwards makes them easily available for use.

8 Claims, 6 Drawing Figures

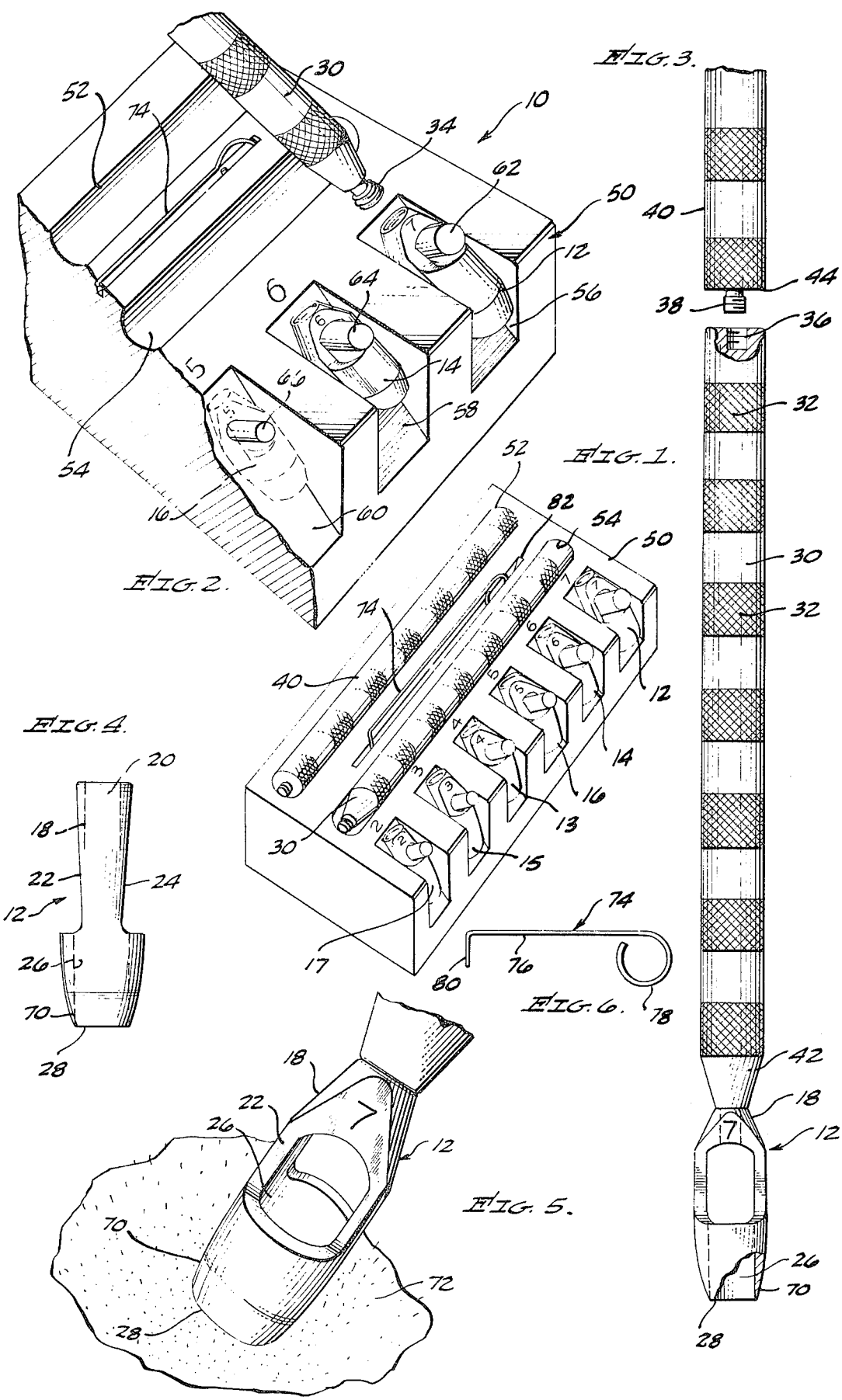

3,949,747

BIOPSY SET

BACKGROUND

This invention is directed to a biopsy set, and particularly a tissue biopsy set which includes a plurality of punches and two handles which can pick up a selected punch, and a probe to remove the tissue from the punch.

In the prior art, tissue biopsy punches in the form of circular cutters have been mounted on a base with the cutting edges unprotected and facing upward. Each punch needed to be removed; for example, by the sterile gloved surgeon, and thereupon the sharp punch could be attached to its handle.

The exposed cutting edge both risked damage to the edge and risked the cutting of the surgeon's glove. When attachment to the base was by screwthread, occasionally the punch was screwed too tight to the base, possibly by sterilization thermal cycling, so that removal became very difficult. Thus the prior tissue biopsy punches have been less than fully satisfactory because of the risk of damage to and by the cutting edges and the handling of the handle and punches in preparation for tissue biopsy use.

SUMMARY

In order to aid in the understanding of this invention, it can be stated in essentially summary form that it is directed to a biopsy set in which a base holds a plurality of receptacles for receiving individual tissue biopsy punches and means for restraining a handle for the punches so that the set can be sterilized and handled together, and the handle can engage the selected tissue punch to selectively lift the tissue punch out of its receptacle for tissue biopsy use.

It is an object of this invention to provide a biopsy set which is convenient and safe to use and which protects the biopsy punch until ready for use. It is another object to provide a tissue biopsy set which can be sterilized as a set, with the punches in a protected position. It is yet another object to provide a tissue biopsy set which contains a plurality of punches, each individually protected, and contains two handles so that a handle can be picked up and engaged into a selected punch to lift the selected punch from its receptacle for use.

Other objects and advantages of this invention will become apparent from a study of the following portion of the specification, the claims, and the attached drawings.

BRIEF DESCRIPTION OF THE DRAWINGS

FIG. 1 is an isometric view of the biopsy set of this invention.

FIG. 2 is an enlarged isometric view of the biopsy set of this invention showing more detail, with parts broken away.

FIG. 3 is a side-elevational view of a tissue biopsy punch with handle engaged and with extension handle in place for engagement, with parts broken away.

FIG. 4 is an edge view of one of the punches.

FIG. 5 is an enlarged view of the punch of FIG. 3, with most of the handle broken away and with the punch shown in position for taking a tissue biopsy.

FIG. 6 is a side-elevational view of the tissue probe.

DESCRIPTION OF THE PREFERRED EMBODIMENT

The biopsy set 10 of this invention consists of a group of six punches, a group of two handles, a probe, and a base to restrain, organize, and hold the punches, handles and probe.

Punch 12 is illustrated in FIGS. 1, 2, 3, 4, and 5. It is one of a set of six punches with additional punches in the set illustrated at 13 through 17 in FIG. 1. There is a sufficient number of punches in the set, preferably each being of a different size, for example, 2 millimeters through 7 millimeters, so that the set contains a punch of desired size. Shank 18 of punch 12 has a threaded opening 20 at its upper end. Shank 18 is recessed on both sides at 22 and 24 to provide access at the shank end to interior bore 26. The exterior of forceps 12 is tapered at 70 to a reduced diameter at the end opposite opening 20 to form circular cutting edge 28. Bore 26 is of uniform diameter from the cutting edge up to the recesses 22 and 24. The punches each have a different diameter bore 26 so that different sized tissue specimens can be taken.

Handle 30, see FIGS. 1, 2, and 3, is of convenient diameter to be held in the fingers and is preferably roughened, as by knurling, throughout its length or through spaced portions of knurling, as at 32, so that it can be readily and manually grasped and handled. The lower end of handle 30 has a male threaded portion 34, see FIG. 2, which can be screwed into the threaded opening 20, as shown in FIG. 3. In this way, handle 30 can be attached and detached from any one of the punches 12 through 17.

The upper end of handle 30 has a threaded opening 36 into which the threaded stud 38 on the lower end of handle 40 can be engaged. Handle 40 is the same as handle 30 so that it can be engaged in a different punch, if desired, or can be engaged in the back of handle 30 to provide a single compound handle of greater length for taking specimens from deep tissue. The forward end of handle 30 adjacent its stud 34 can be tapered, as at 42, to provide smooth appearance. On the other hand, handle 40 can be provided with a square corner 44 to fit against the upper end of handle 30, if desired. Further, they can be identical in this feature, as well as throughout the remaining features of the handles.

Base 50, like the handles 30 and 40, is a substantially rigid material which is sterilizable. The punches 12 through 17 need to retain a sharp edge as well as be sterilizable, and thus they are preferably metallic. Similarly, the handles and base 50 are also preferably metallic. Base 50 is sufficiently long to receive all of the punches in the set. On its top surface, it contains recesses 52 and 54 which are sufficiently long to receive the handles 30 and 40 and are sufficiently deep to fairly well restrain the handles; however the recesses are sufficiently shallow that the handles can be manually picked up out of the recesses. There are six receptacles, one for each punch. Receptacles 56, 58, and 60, see FIG. 2, are formed as separate angular slots extending through a corner of the base from the top surface to the side surface. Each receptacle is sufficiently wide to receive a punch so that, when a punch is placed therein, it is completely recessed below the top surface of the base and recessed back of the side surface of the base, as shown in FIGS. 1 and 2. Holding pins 62, 64, and 66 are respectively located in the receptacles 56, 58, and 60 and extend upward normal to the bottom surface of each receptacle. As previously discussed, each punch has an opening 68 therethrough which is the result of the cutback sides 22 and 24 of shank 18 intersecting with the interior bore 26. The distance across opening 68 is thus substantially equal to, but slightly less than bore 26. Holding pin 62 is designed to fairly closely fit within opening 68. The width of the receptacle 58 between its walls is such that, when punch 12 is fit on holding pin 62, the taper 70 which forms cutting edge 28 is sufficient that the cutting edge cannot touch either of the receptacle walls. Furthermore, the length of opening 68 in the axial direction of bore 26, in association with holding pin 62, is such that the cutting edge 28 cannot touch the bottom of receptacle 56, even though the punch can be somewhat tilted on holding pin 62.

Probe 74 has a shank 76 which carries handle 78 on one end and probe point 80 on the other. Probe 74 can be made of metal wire, as shown. It is stored in slot 82 in base 50, see FIGS. 1 and 2.

In use, each of the punches is in place on its holding pin in its receptacle, the handles are in their respective recesses 52 and 54, and punch 74 is in its slot 82. The entire structure is sterilized as a set. When being placed in use, one of the handles can be manually picked out of its recess and threaded into the selected punch, as shown in FIGS. 1 and 2. When installed in the punch, the punch can be lifted off of its holding pin and out of its recess by manipulation of the handle. When the surgeon holds the punch against the skin 72, as shown in FIG. 5, a disc of epidermis is cut out by cutting edge 28. This epidermis remains in the punch when the punch is removed from the biopsy site. The tissue obtained by this biopsy is placed for examination by removing it from the bore of the punch by use of probe 74. Probe point 80 is inserted downward through bore 26 to force out the tissue.

If a longer handle is necessary, the second handle can be inserted into the back end of the first one. If more than one punch must be used in a procedure, the second handle can be used in the second punch when a long handle is not required, or the first punch can be returned to its receptacle, its handle removed and screwed into the next selected punch, and then that next selected punch can be removed from its receptacle and employed in tissue biopsy.

Thus, a unitary structure which cooperates in storage, sterilization, being ready for use, and protecting the punches prior to actual immediate use, protection of surroundings from the sharp edges of the punches, and convenient manual use in sterilized conditions is achieved.

This invention having been described in its preferred embodiment, it is clear that it is susceptible to numerous modifications and embodiments within the ability of those skilled in the art and without the exercise of the inventive faculty. Accordingly, the scope of this invention is defined by the scope of the following claims.

What is claimed is:
1. A biopsy set comprising:
   a plurality of tissue biopsy punches each having a sharp edge, a biopsy punch handle, attachment means on each of said tissue biopsy punches and on said biopsy punch handle for selectively engaging said biopsy punch handle into one of said tissue biopsy punches;
   a base of sterilizable material, said base having a top and a side, recess means in said top for disengageably receiving said biopsy punch handle;
   a plurality of receptacle slots in said base angularly directed with respect to said top and intersecting both said top and said side, a holding pin extending into each of said slots for receiving one of said tissue biopsy punches and retaining a biopsy punch within each of said receptacles with its sharp edge away from said base so that said base acts as a holder for said biopsy punch handle and all of said tissue biopsy punches.

2. The biopsy set of claim 1 wherein each of said receptacle slots has a bottom wall and said bottom wall intersects both said top and said side, said holding pin being secured in said bottom wall, each said tissue biopsy punch having a transverse opening therethrough with said holding pin engaging said transverse opening to hold each said tissue biopsy punch in its receptacle slot.

3. The biopsy set of claim 1 wherein each of said tissue biopsy punches has an external cutting edge thereon, and each of said tissue biopsy punches is positioned within its receptacle slot so that each tissue biopsy punch cutting edge is within the confines of its receptacle slot.

4. The biopsy set of claim 3 wherein each said biopsy tissue punch has an axis and said attachment means is on said axis for attaching said biopsy punch handle.

5. The biopsy set of claim 4 wherein said attachment means is a threaded male stud on said handle and a corresponding threaded opening in said punch on the axis thereof.

6. The biopsy set of claim 5 wherein said handle is a first handle and further including a second handle and attachment means on said first handle and said second handle so that said second handle can be attached to said first handle.

7. The biopsy set of claim 6 wherein said attachment means between said first handle and said second handle is the same as the attachment means between said punch and said handle.

8. The biopsy set of claim 1 wherein each of said receptacle slots has a bottom wall and said bottom wall intersects both said top and said side, said holding pin being secured in said bottom wall, each said tissue biopsy punch having a transverse opening therethrough with said holding pin engaging said transverse opening to hold each said tissue biopsy punch in its receptacle slot.

* * * * *